United States Patent [19]
Ochi et al.

[11] Patent Number: 5,950,634
[45] Date of Patent: Sep. 14, 1999

[54] METHOD FOR ASSESSING OXIDATIVE STRESS AND ITS CONTROL IN HUMANS

[75] Inventors: Hirotomo Ochi, Fukuroi, Japan; Richard G Cutler, Baltimore, Md.

[73] Assignee: Nikken Foods Co., Ltd., Japan

[21] Appl. No.: 08/979,256

[22] Filed: Nov. 26, 1997

[30] Foreign Application Priority Data

Nov. 29, 1996 [JP] Japan .................................. 8-320199

[51] Int. Cl.$^6$ .................................................. A61B 19/00
[52] U.S. Cl. ................................ 128/898; 435/25; 426/73
[58] Field of Search .............................. 426/73; 435/25; 514/54; 128/898

[56] References Cited

U.S. PATENT DOCUMENTS 4,023,276  5/1977  Furukowa et al. ........................ 33/1 C

FOREIGN PATENT DOCUMENTS 2 518 283  6/1983  France .
43 28 639  3/1995  Germany .
555 064  10/1974  Switzerland .
614 300  11/1979  Switzerland .

*Primary Examiner*—Max Hindenburg
*Assistant Examiner*—Brian Szmal
*Attorney, Agent, or Firm*—Wenderoth, Lind & Ponack, L.L.P.

[57] ABSTRACT

A chart used for assessing oxidative stress is prepared, wherein a numerical figure representing the degree of excess or deficiency of an indicator substance indicating oxidative stress in humans is shown in the ordinate, and a numerical figure corresponding to the standard value recovered from normal subjects is also shown in the ordinate, while the items of such indicator substances are grouped in damaging substances, water-soluble antioxidants, fat-soluble antioxidants, and antioxidant enzymes to be shown in the abscissa. By numerically representing the ratio of the measured value of each indicator substance in a test subject to the standard value and recording the resulting numerical figure on the chart, the degree of excess or deficiency of the indicator substance indicating the extent of oxidative stress in humans is collectively shown in the chart, whereby the degree of excess or deficiency of the indicator substance in a test subject can be analyzed in a simple procedure.

6 Claims, 7 Drawing Sheets

CHART FOR ASSESSING OXIDATIVE STRESS

CHART FOR ASSESSING OXIDATIVE STRESS

CHART FOR ASSESSING OXIDATIVE STRESS

CHART FOR ASSESSING OXIDATIVE STRESS

CHART FOR ASSESSING OXIDATIVE STRESS

METHOD FOR ASSESSING OXIDATIVE STRESS AND ITS CONTROL IN HUMANS

BACKGROUND OF THE INVENTION

1. Field of the Invention

The present invention relates to a method for assessing oxidative stress whereby the degree of excess or deficiency of an indicator substance indicating the extent of oxidative stress in humans can be determined and assessed in a simple manner so as to maintain health and control aging in a test subject through appropriate supplement of the test subject with the antioxidant detected as deficient.

2. Description of the Related Art

No method for assessing oxidative stress has been known, conventionally, where deficient antioxidants in a test subject are collectively shown. Therefore, it has been difficult to detect deficient antioxidants in a test subject and supplement the test subject with appropriate antioxidants. Additionally, conventional antioxidants include water-soluble antioxidants, fat-soluble antioxidants and antioxidant enzymes with micronutrient minerals as components. Therefore, it has been very difficult to supplement such test subject with a just required group of antioxidants.

SUMMARY OF THE INVENTION

In such circumstances, the present invention can overcome the conventional problems described above, by providing a method for assessing oxidative stress whereby antioxidants deficient in a test subject can be detected and analyzed collectively. If a test subject is appropriately supplemented with an antioxidant having detected as deficient and being in the form of an antioxidant supplement produced for each group of natural antioxidants on the basis of the result of assessment, antioxidants of a group just required for the test subject can be supplemented.

More specifically, the present invention provides a method for assessing oxidative stress in humans comprising a step of preparing a chart for assessing oxidative stress wherein a numerical figure representing the degree of excess or deficiency of an indicator substance indicating oxidative stress in humans is shown in the ordinate, and a numerical figure corresponding to the standard value recovered from normal subjects is also shown in the ordinate, while in the abscissa are shown the items of such indicator substances as grouped in damaging substances, water-soluble antioxidants, fat-soluble antioxidants and antioxidant enzymes. And then, recording the ratio of the measured value of a damaging substance, a water-soluble antioxidant, a fat-soluble antioxidant, or an antioxidant enzyme from the serum measurement of a test subject to the standard value thereof in normal subjects on the before described chart for assessing oxidative stress, all indicator substances indicating the extent of oxidative stress in humans including the ratio of oxidative stress in the test subject relative to normal subjects, namely the health state and the progress of aging, can be determined and assessed collectively.

The degree of excess or deficiency of an indicator substance indicating the extent of oxidative stress, which is represented in the ordinate as described above, is identified as follows; the mean value of the measured values of an indicator substance in 150 normal subjects (men and women) is defined as standard value of 100. Then, a numerical figure representing the ratio of excess or deficiency of the indicator substance to the standard value is shown in the ordinate. For example, when the amount of an indicator substance in a test subject is two fold the standard value, the numerical figure of '200' is recorded in the column of the item of the indicator substance in the abscissa; in contrast, when the amount thereof is half of the standard value, the numerical figure '50' is recorded in the column of the item of the indicator substance in the abscissa. These figures are graphically shown in the chart for assessing oxidative stress.

As the indicator substance for assessing oxidative stress, use may be made of a group consisting of substances damaging fat, protein and glucose, pro-oxidants, and total antioxidants, in addition to damaging substances including nucleic acid, water-soluble antioxidants, fat-soluble antioxidants and antioxidant enzymes, which are represented in the columns of the items thereof in the abscissa. The group consisting of substances damaging fat, protein, and glucose, pro-oxidants and total antioxidants can work to assist the assessment of oxidative stress. Therefore, these may be effective for assessing oxidative stress in a comprehensive manner.

The levels of substances damaging fat, protein and glucose, water-soluble antioxidants, fat-soluble antioxidants, antioxidant enzymes, pro-oxidants and total antioxidants in the body have strong correlation individually with the health state, aging and adult diseases in humans. Rather than independently examining these conditions, a comprehensive determination and assessment of conditions using the methods for assessing oxidative stress in accordance with the present invention will provide a more effective health management and aging control strategy.

As has been described above, in any case, the indicator substances for assessing the extent of oxidative stress are classified into the group consisting of substances damaging fat, protein and glucose, pro-oxidants, total antioxidants, water-soluble antioxidants, fat-soluble antioxidants, and antioxidant enzymes. Then, it can be clearly shown which antioxidant is deficient in a test subject. As a consequence, the test subject can be supplemented appropriately with the antioxidant detected as deficient.

As shown below in Table 1, each indicator substance has a standard range. The term 'standard range' means a normal range of measured values from 150 apparently normal men and women. It is believed that a test subject has no specific health problem if a measured value of the indicator substance in the test subject falls within the standard range. The standard range of each indicator substance can be arranged above or below the standard value of 100 [the mean value of each indicator substance in 150 normal men and women samples is defined as the FIG. 100 in the ordinate] in the chart for assessing oxidative stress. If a standard range is organized in such a manner as described above, the degree of excess or deficiency of each indicator substance in the test subject can be determined and assessed instantly.

Since the standard range of each indicator substance has a different scale units, the standard ranges of individual indicator substances cannot be arranged linearly. For example, the standard range of indicator substance No.1 [malondialdehyde] is from 14.0 to 26.0 $\mu$gM, with a variation of 12.0 $\mu$M between the upper and lower limits; the standard range of the indicator substance No.25 [thiol] is from 14.0 to 19.0 $\mu$M, with a variation of 5.0 $\mu$M between the upper and lower limits. Therefore, the standard range of indicator substance No.1 [malondialdehyde], with the mean on the standard value 100, has a bigger spread than the standard range of indicator substance No.25 [thiol].

In summary, the mean values of measured values of each indicator substance in 150 normal men and women samples, is defined as standard value of 100. On such a basis, the upper limit and lower limit of the standard range of each of the indicator substance is numerically defined and recorded as a point, above and below the standard value. The resulting recorded points are linked together to arrive at an overall standard range.

As described above, the standard range individually varies depending on each indicator substance. Therefore, the standard range is shown as the range of 100−α to 100+α in the chart for assessing oxidative stress. Since the standard range should vary depending on each indicator substance, the overall standard range of these indicator substances need to be shown in a curve. In the annexed charts, the overall standard range is shown linearly for each comprehension.

Apart from the standard range, three additional categories, namely, safety range, normal range and abnormal range are also grouped and defined. By such categorisation, not only the degree of excess or deficiency of an antioxidant in a test subject but also the health state and progress in aging can be determined and assessed instantly. Herein, the category identified as the safety range is remarkably different from the standard range (represented as corrected values) in numerical figure. But it is believed that numerical figures (of corrected values) in the safety range do not suggest any pathological problem. The normal range is a group comprising the standard range and the safety range. Furthermore, the abnormal range is distinctly different from the standard range (in being elevated or depressed than the standard range), thus suggesting some pathological influence.

In addition, the present invention proposes that the indicator substances should be configured as described below in the charts for assessing oxidative stress.

Damaging substances consist of at least one or more serum components such as malondialdehyde, 4-hydroxy nonenal, hydroperoxide, 8 hydroxy deoxyguanosine (nucleic acid) in urine, and a mixture of malonialdehyde and 4-hydroxy nonenal. The amounts of these substances in body fluids reveal the degree of oxidative damage, and by comparing the amounts of these substances in serum withdrawn from a test subject with the standard values thereof, the progress of oxidative damage in humans can be assessed.

One or more complexes of iron and ferritin are known as pro-oxidants contributing to precursor risk for oxidative stress. By comparing the amounts of these substances in serum withdrawn from a test subject with the standard values thereof, the potential possibility of oxidative stress in humans can be assessed.

Water-soluble antioxidants in the blood consist of at least one or more of the following; ascorbic acid, thiols, uric acid and bilirubin. By comparing the levels of these substances in serum withdrawn from a test subject with the standard values thereof, the antioxidant potential in humans can be assessed.

Fat-soluble antioxidants in the blood consist of at least one or more of the following: lutein, zeaxanthine, cryptoxanthin, lycopene, carotenes, retinol and tocopherols. By comparing the levels of these substances in serum withdrawn from a test subject with the standard values thereof, the antioxidant potency in humans can be assessed.

The group comprising of substances damaging fat, protein, and glucose consists of at least one or more of the following: cholesterol, triglyceride, albumin, total protein, globulin and glucose. These have properties suggesting biochemical indicators in blood, and by comparing the amounts of these substances in serum withdrawn from a test subject with the standard values thereof, the biological balance and pathological relation can be assessed.

Antioxidant enzymes include coenzyme Q10, superoxide dismutase, catalase and glutathione peroxidase. These have oxygen radical quenching potency, and by comparing the amounts of these substances in serum withdrawn from a test subject with the standard values thereof, the protective potency in humans can be assessed.

The total antioxidant substance as one of the indicator substances has a property suggesting the total oxygen radical quenching potency in serum, and by comparing the amounts of these substances in serum withdrawn from a test subject with the standard values thereof, the total oxygen radical quenching potency in humans can be assessed.

On the basis of the method for assessing oxidative stress in accordance with the present invention, a water-soluble substance, a fat-soluble substance and an antioxidant enzyme, deficient in a test subject, can be determined in a simple manner. Based on this outcome, either an antioxidant supplement singly consisting of natural products containing water-soluble antioxidants, antioxidant supplement singly consisting of natural products containing fat-soluble antioxidants, or antioxidant supplement singly consisting of natural products containing micronutrient minerals as components of antioxidant enzymes can be incorporated in the diet of a test subject. Thus, to control the oxidative stress, the test subject can be readily and simply supplemented with the antioxidant detected as deficient.

More specifically, by individually preparing antioxidant supplements singly comprising of natural products containing water-soluble antioxidants and at least one or more of tea catechin, teas, fruits, green vegetables and beans, antioxidant supplements singly comprising of natural products containing fat-soluble antioxidants and at least one of beans, green vegetables, seeds or colored vegetables or antioxidant supplement singly comprising of natural products containing micronutrient minerals as components of antioxidant enzymes and comprising fish, shell fish, milk product, yeast, green tea, sea weed or beans, and then making the test subject incorporate these antioxidant supplements to supplement water-soluble antioxidants, fat-soluble antioxidants and the antioxidant enzymes, all of which are detected as deficient, whereby the antioxidants detected as deficient in the test subject can be supplemented to control the oxidative stress.

Because conventional antioxidants consist of a mixture of compounds such as water-soluble antioxidants, fat-soluble antioxidants, and micronutrient minerals as components of antioxidant enzymes, necessary antioxidants cannot be exactly supplemented independently. But, if antioxidant supplements are individually prepared for water-soluble antioxidants, fat-soluble antioxidants or micronutrient minerals as the component of antioxidant enzymes as described above, each antioxidant just needed for a test subject can be readily and simply supplemented exactly on the basis of the assessment outcome from the chart for assessing oxidative stress, in accordance with the present invention.

The combination of natural products as described above is not definite, but essentially, the combination is composed of natural products with the same function. The antioxidant supplement can supplement antioxidants likely to be deficient in daily diet, and even the excess intake thereof cannot cause any side effect. Therefore, these supplements can be used safely for all age groups, including children and elderly.

How to use the method for assessing oxidative stress in accordance with the present invention and how to assess the degree of oxidative stress in a test subject is described below.

The chart used for assessing oxidative stress as shown in FIG. 1 is prepared first. More specifically, numerical figures from 0 to 200 are scaled in the ordinate, while the indicator substance No. is shown in the abscissa, so as to record the data of each indicator substance of a test subject in the abscissa. The numerical figure of the standard value of each indicator substance (mean value from 150 normal men and women) is defined as 100 in the ordinate. For example, a numerical FIG. 50 may be used as the figure corresponding to the standard value, but only if the numerical FIG. 100 should correspond to the standard value, the ratio of the measured value of each indicator substance in a test subject to the standard value can be conveniently represented in percentage.

By the method described above, the upper and lower limits of each standard range as shown in Table 1 is then numerically represented at the same ratio as the ratio of the mean of the measured values of 150 normal men and women is corrected or converted to the numerical FIG. 100. Then, the resulting numerical figures are individually recorded as a point per each indicator substance. In the next step, these upper and lower limits are independently linked together to formulate an overall standard range. In the ordinate, numerical figures of 100−α and 100+α are shown in right positions, almost corresponding to the upper and lower limits respectively, of each standard range.

So as to propose a more readily observable analytical view, the standard range can be colored as in the slashed area in the chart of FIG. 1. As in the chart of FIG. 1, a comment of "very low" and "very high" is assigned to the figure of "25" and "175" each respectively on the ordinate.

In using the chart for assessing oxidative stress, the amount of each indicator substance in serum withdrawn from a test subject is measured and corrected (or converted) on the basis of the standard value defined as 100, which is then recorded in the chart for assessing oxidative stress. The recorded corrected (or converted) value of each indicator substance can be represented in bar graph as shown in the chart of FIG. 1, whereby an indicator substance, in excess or deficient, can be readily determined. Such a graph can be represented not only in a bar graph as shown in FIG. 1, but also in zig zag graph; some of such indicator substances may satisfactorily be represented graphically.

FIG. 2 is a chart used for assessing oxidative stress, whereby it is readily viewed as to where the corrected (or converted) value of each indicator substance, as recorded in the chart of FIG. 1, is localized among the standard range, normal range, safety range and abnormal range. As in the chart of FIG. 1, numerical figures from 0 to 200 are scaled in the ordinate, and the numerical FIG. 100 is defined as the standard value of each indicator substance (mean value of 150 normal men and women). In the abscissa, the numbers of indicator substances are scaled so as to record the corrected value of each indicator substance. The chart for assessing oxidative stress as shown in FIG. 2, assess only damaging substances and antioxidants (water-soluble antioxidants and fat-soluble antioxidants). Additionally, a chart for only damaging substances or a chart for only antioxidants (water-soluble antioxidants and fat-soluble antioxidants) can be prepared as well.

So as to make appropriate assessment, herein, at least indicator substance Nos. corresponding to damaging substances, water-soluble antioxidants, fat-soluble antioxidants and antioxidant enzymes, are essentially scaled for assessment; preferably, indicator substance Nos. of damaging substances, pro-oxidants, total antioxidants, water-soluble antioxidants, fat-soluble antioxidants, a group of fat, protein, nucleic acid and glucose, and antioxidant enzymes are scaled correspondingly to the chart of FIG. 1 for assessment thereof The categories such as "safety range" assigned to individual ranges in the chart for assessing oxidative stress in FIG. 2 are as same as described above. In the method for assessing oxidative stress using the chart of FIG. 2, the degree of oxidative stress in a test subject can be determined by observing where the numerical figure of each indicator substance in the test subject (numerical figure of the corrected or converted value of the measured value of each indicator substance in the test subject on the basis of the standard value of 100) is localized among the three categories, namely, standard range, safety range and abnormal range.

The detection of the degree of oxidative stress in a test subject by using the charts for assessing oxidative stress as shown in FIG. 2 can be carried out at the following five stages.

First stage (at a state with 'hypothetically zero' oxidative stress)
Second stage (at a state with minimal oxidative stress)
Third stage (at a state with weak oxidative stress)
Fourth stage (at a state with regular oxidative stress)
Fifth stage (at a state with severe oxidative stress)
Each of these five stages are explained below.

First Stage (at a state with 'hypothetically zero' oxidative stress)

As shown in the chart of FIG. 3, the corrected values of damaging substances and pro-oxidants are within the normal ranges; and the corrected values of antioxidants (water-soluble antioxidants and fat-soluble antioxidants) are also within the normal ranges. Additionally, the corrected values of other indicator substances are also within the standard ranges. More specifically, the corrected values of individual indicator substances of damaging substances, pro-oxidants, antioxidants (water-soluble antioxidants and fat-soluble antioxidants) are all recorded within the normal ranges (comprising of standard ranges and safety ranges); the corrected values of the remaining indicator substances are also within the standard ranges, with no corrected value of any indicator substance, to be recorded within the abnormal range thereof Second Stage (at a state with minimal oxidative stress)

As shown in the chart of FIG. 4, corrected values of damaging substances and pro-oxidants are shown, for example, within a range of about 110 to 130; corrected values of antioxidants (water-soluble antioxidants and fat-soluble antioxidants) are, for example, within a range of about 70 to 90; corrected values of the remaining indicator substances are, for example, within a range of about 50 to 70 or within a range of about 130 to 160. Thus, corrected values of individual indicator substances, namely damaging substances, pro-oxidants, and antioxidants (water-soluble antioxidants and fat-soluble antioxidants), are recorded slightly within the abnormal ranges thereof. Additionally, corrected values of the remaining indicator substances are recorded within the safety ranges in addition to within the standard ranges.

By detecting an antioxidant deficient in a test subject on the basis of the method for assessing oxidative stress using the chart of FIG. 1, and effectively supplementing the test subject with the antioxidant detected as deficient by using an antioxidant supplement produced singly from natural products containing water-soluble antioxidants, an antioxidant supplement produced singly from natural products containing fat-soluble antioxidants, or an antioxidant supplement produced singly from natural products containing micronutrient minerals as the component of antioxidant enzymes, the corrected value of the antioxidant can readily by shifted toward the standard range, as shown by the arrow in the chart of FIG. 4. It is also possible to prescribe an effective treatment on the basis of the assessment outcome by this method, so that the values of damaging substances and pro-oxidants might shift toward the standard ranges thereof, as shown in the chart of FIG. 4.

Third Stage (at a state with weak oxidative stress)

As shown in the chart of FIG. 5, corrected values of damaging substances and pro-oxidants are shown, for example, within a range of about 130 to 160; corrected values of antioxidants (water-soluble antioxidants and fat-soluble antioxidants) are, for example, within a range of about 50 to 70; corrected values of the remaining indicator substances are, for example, within a range of about 70 to 90 or within a range of about 110 to 130. Thus, corrected values of individual indicator substances, namely damaging substances, pro-oxidants and antioxidants (water-soluble antioxidants and fat-soluble antioxidants) are recorded slightly within the abnormal ranges thereof. Additionally, corrected values of the remaining indicator substances rather than being within the standard ranges are recorded slightly within the safety ranges.

As in the second stage, similarly herein, by detecting an antioxidant deficient in a test subject on the basis of the method for assessing oxidative stress using the chart of FIG. 1 and effectively supplementing the test subject with the antioxidant detected as deficient by using an antioxidant supplement produced singly from natural products containing water-soluble antioxidants, an antioxidant supplement produced singly from natural products containing fat-soluble antioxidant, or an antioxidant supplement produced singly from natural products containing micronutrient minerals as the component of antioxidant enzymes, the corrected value of the antioxidant can readily be shifted toward the standard range, as shown by the arrow in the chart of FIG. 5. It is also possible to prescribe an effective treatment on the basis of the assessment outcome on the method, so that the corrected values of damaging substances and pro-oxidants might shift toward the standard ranges thereof, as shown in the chart of FIG. 5.

Fourth Stage (at a state with regular oxidative stress)

As shown in the chart of FIG. 6, corrected values of damaging substances and pro-oxidants are, for example, shown within a range of about 160 to 180; corrected values of antioxidants (water-soluble antioxidants and fat-soluble antioxidants) are, for example, within a range of about 30 to 50; corrected values of the remaining indicator substances are, for example, within a range of about 50 to 70 or within a range of about 130 to 160; i.e., corrected values of individual indicator substances, namely damaging substances, pro-oxidants and antioxidants (water-soluble antioxidants and fat-soluble antioxidants) are recorded at positions further from the standard ranges, but within the abnormal ranges thereof. Additionally, corrected values of the remaining indicator substances are recorded at positions closer to the abnormal ranges, but within the safety ranges.

As in the second stage, similarly herein, by detecting an antioxidant deficient in a test subject on the basis of the chart for assessing oxidative stress using the chart of FIG. 1, and effectively supplementing the test subject with the antioxidant detected as deficient by using an antioxidant supplement produced singly from natural products containing water-soluble antioxidants, an antioxidant supplement produced singly from natural products containing fat-soluble antioxidants or an antioxidant supplement produced singly from natural products containing micronutrient minerals as the component of antioxidant enzymes, the corrected value of the antioxidant can readily be shifted toward the standard range, as shown by the arrow in the chart of FIG. 6. It is also possible to prescribe an effective treatment on the basis of the assessment outcome from the chart, so that the corrected values of damaging substances and pro-oxidants might shift toward the standard ranges thereof, as shown in the chart of FIG. 6, on the basis of the assessment outcome on the assessment chart.

Fifth Stage (at a state with severe oxidative stress)

As shown in the chart of FIG. 7, corrected values of damaging substances and pro-oxidants are, for example, shown within a range of about 180 or more; corrected value of antioxidants (water-soluble antioxidants and fat-soluble antioxidants) are, for example, within a range of about 30 or less; corrected values of the remaining indicator substances are, for example, within a range of about 50 or less or within a range of about 160 or more; i.e., corrected values of individual indicator substances, namely damaging substances, pro-oxidants and antioxidants (water-soluble antioxidants and fat-soluble antioxidants) are recorded at positions furthest from the standard ranges but within the abnormal ranges thereof. Additionally, corrected values of the remaining indicator substances are not recorded within the safety ranges, but within the abnormal ranges furthest from the safety ranges.

As in the second stage, similarly herein, by effectively supplementing the test subject with the antioxidant detected as deficient by using the chart for assessing oxidative stress as shown in FIG. 1, and an antioxidant supplement produced singly from natural products containing water-soluble antioxidants, an antioxidant supplement produced singly from natural products containing fat-soluble antioxidants, or an antioxidant supplement produced singly from natural products containing micronutrient minerals as the component of antioxidant enzymes, the corrected value of the antioxidant can readily by shifted toward the standard range, as shown by the arrow in the chart of FIG. 7. It is also possible to prescribe an effective treatment on the basis of the assessment outcome from the chart, so that the corrected values of damaging substances and pro-oxidants might shift toward the standard ranges thereof, as shown in the chart of FIG. 7, on the basis of the assessment outcome on the assessment chart.

As has been described above, in accordance with the present invention, antioxidant components deficient in a test subject can be detected and assessed collectively in a simple manner on the basis of the chart for assessing oxidative stress. The degree of excess or deficiency of the antioxidant components in the test subject can be graphically shown for a comprehensive view in a simple and definite manner. Which range the state of antioxidant components in the test subject is localized among the standard range, safety range and abnormal range, can be determined generally in a simple step. Accordingly, the general health state and degree of aging in the test subject can be assessed appropriately.

Based on the detected outcome, the test subject can effectively be supplemented with an appropriate amount of an antioxidant supplement produced singly from natural products containing water-soluble antioxidants, an antioxidant supplement produced singly from natural products containing fat-soluble antioxidants, or an antioxidant supplement produced singly from natural products containing micronutrient minerals as the component of antioxidant enzymes, thereby the oxidative stress in the test subject can be controlled easily.

Thus, this method is effective for controlling diseases and aging for which oxidative stress is a major factor.

Furthermore, the substances to be used are all derived from natural products, without concerns against side effects or excess intake. Therefore, such substances can be effectively used in a wide rage by humans of all age groups, from children to elderly.

DETAILED DESCRIPTION OF THE PREFERRED EXAMPLES

Representative examples of the present investion is described below, with reference to the annexed drawings.

EXAMPLE 1

Figure 1:
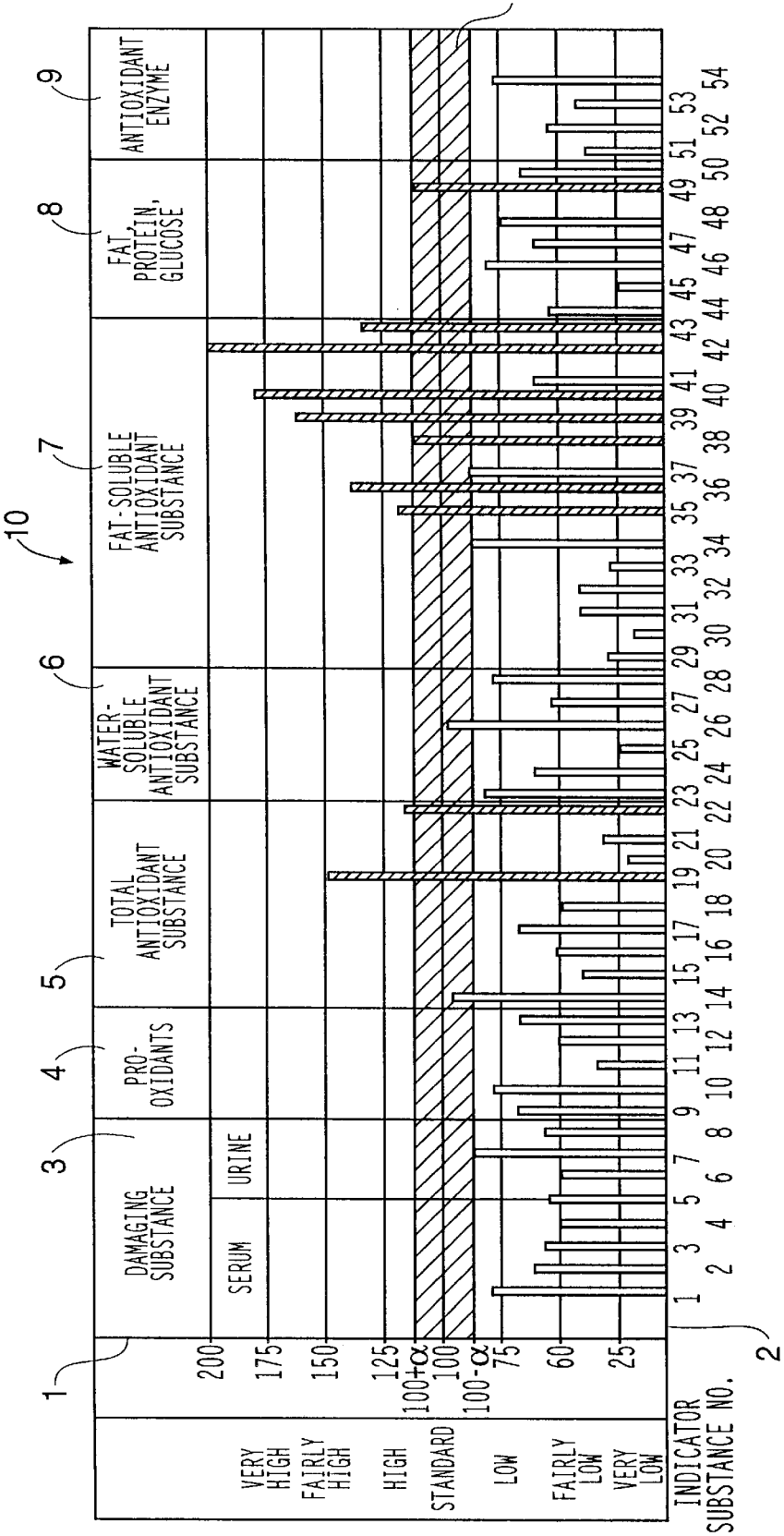
FIG. 1 is a chart depicts histograms representing the corrected values of individual indicator substances in a test subject on the chart used for assessing oxidative stress in accordance with the present invention.

FIG. 1 depicts the chart 10 employed in the method for assessing the oxidative stress, pertaining to the present invention. In the ordinate 1, the degree of excess or deficiency of an indicator substance is shown in numerical figures up to 200. Herein, the numerical FIG. 100 corresponds to the standard value (mean value of each indicator substance in 150 normal men and women). The representation in the ordinate is not limited to the representation in the present example, but it is possible to use the numerical FIG. 50 as the standard value and use figures up to 100 there on. Otherwise, it is also possible to define the upper limit as 300 or 400; i.e., in recording the measured value of each indicator substance as a ratio to the mean value thereof in 150 normal men and women, on the assessment chart 10, the ordinate should be scaled to define the standard value as one numerical figure, so as to propose an instantaneous view of the degree of excess or deficiency of the indicator substances in a simple fashion.

On the assessment chart 10, the standard range of each indicator substance is defined and colored within standard range of 11 of 100−α to 100+α, whereby the standard range is apparently observable.

Individual indicator substance Nos. are shown in the bottom of the abscissa 2. In the upper part of the abscissa, herein, the items of indicator substances including damaging substance 3, pro-oxidants 4, total antioxidant 5, water-soluble antioxidant 6, fat-soluble antioxidant 7, group of fat (substances damaging fat), protein and glucose 8, and anti-oxidant enzyme 9 are shown conveniently to propose quick glance regarding which indicator substance is in excess or deficient. In the present example, more specifically, the indicator substance Nos. 1 to 8 are grouped in damaging substance; the substance Nos. 9 to 13 are grouped in pro-oxidants; the indicator substance Nos. 14 to 22 are grouped in total antioxidants.

When using the chart 10 for assessing oxidative stress, the amounts of individual indicator substances contained in serum withdrawn from a test subject are measured and corrected (converted) on the basis of the standard value defined as 100. The resulting numerical figures (corrected values) are recorded in the indicator substance Nos. on the assessment chart 10. In the example of FIG. 1, for example, the measured value in the test subject of the indicator substance corresponding to the indicator substance No.4 (hydroperoxide FOX) corresponds to 60% of the standard value.

On the assessment chart 10, corrected values are simply recorded as points, but graphically shown in histograms, as shown in the chart of FIG. 1, whereby the degree of excess or deficiency of each indicator substance can be identified more simply. In the histograms shown in the chart of FIG. 1, the slashed areas show that the indicator substances are above the standard ranges.

Because the graphs are drawn by using corrected values of indicator substances, provided that the standard values thereof are defined as 100, the degree of excess or deficiency of each indicator substance can be readily determined. The degree of excess or deficiency of each indicator substance also represents the degree of excess or deficiency of a group to which the substance belongs. Thus, individual antioxidants detected as deficient can be supplemented appropriately on the basis of assessment chart 10, for assessing oxidative stress.

Table 1 presents the names of indicator substances and their corresponding numbers (1 to 54), based on the assessment chart 10 in FIG. 1, and the standard ranges of the individual indicator substances (normal ranges in numerical figure of individual indicater or substances in 150 normal men and women).

TABLE 1

| Indicator substance Nos. in charts | Indicator Substances | Standard ranges |
|---|---|---|
| 1 | malondialdehyde [MDA] ($\mu$M) | 14.0–26.0 |
| 2 | free MDA ($\mu$M) | 0.5–2.5 |
| 3 | hydroperoxide [LPO assay] ($\mu$M) | 1.6–2.4 |
| 4 | hydroperoxide [FOX assay] ($\mu$M) | 0.3–3.2 |
| 5 | thiobarbituric acid reactive substance [TBARS] ($\mu$M) | 0.07–10.2 |
| 6 | TBARS/creatinine | 0.0007–0.204 |
| 7 | 8-hydroxy deoxyguanosine [8-OH dG] (ng/ml) | 3.0–22.0 |
| 8 | MDA + 4-hydroxy nonenal [4-H NE] ($\mu$M) | 5–15 |

TABLE 1-continued

| Indicator substance Nos. in charts | Indicator Substances | Standard ranges |
|---|---|---|
| 9 | iron ($\mu$g/dl) | 35–140 |
| 10 | available iron-binding capacity [AIBC] ($\mu$g/dl) | 130–375 |
| 11 | total iron-binding capacity [TIBC] ($\mu$g/dl) | 245–400 |
| 12 | iron saturation (ng/ml) | 13–45 |
| 13 | ferritin (ng/ml) | 30–480 |
| 14 | total oxygen radical absorbance capacity [ORAC] (whole) ($\mu$M) | 3300–5000 |
| 15 | 95% fraction of total ORAC (whole) ($\mu$M) | 300–600 |
| 16 | 50% fraction of total ORAC (whole) ($\mu$M) | 1500–2300 |
| 17 | total ORAC (aqueous) ($\mu$M) | 480–1000 |
| 18 | 95% fraction of total ORAC (aqueous) ($\mu$M) | 150–510 |
| 19 | 50% fraction of total ORAC (aqueous) ($\mu$M) | 310–750 |
| 20 | total ORAC (lipid) ($\mu$M) | 220–550 |
| 21 | 95% fraction of total ORAC (lipid) ($\mu$M) | 1.5–8.0 |
| 22 | 50% fraction of total ORAC (lipid) ($\mu$M) | 65–200 |
| 23 | lipid peroxidation inhibition activity (LPIC) (%) | 45–85 |
| 24 | ascorbate ($\mu$g/ml) | 7.0–26.5 |
| 25 | thiol ($\mu$M) | 14–19 |
| 26 | uric acid (mg/dl) | 3.5–7.7 |
| 27 | C-bilirubin (mg/dl) | 0–0.3 |
| 28 | total bilirubin (mg/dl) | 0.1–1.2 |
| 29 | lutein ($\mu$g/ml) | 0.06–0.64 |
| 30 | zeaxanthin ($\mu$g/ml) | 0.018–0.16 |
| 31 | $\beta$-cryptoxanthin ($\mu$g/ml) | 0.0069–0.26 |
| 32 | lycopene ($\mu$g/ml) | 0.02–0.72 |
| 33 | $\alpha$-carotene ($\mu$g/ml) | 0.0062–0.38 |
| 34 | $\beta$-carotene ($\mu$g/ml) | 0.078–0.75 |
| 35 | retinol ($\mu$g/ml) | 0.36–1.26 |
| 36 | retinol palmitate ($\mu$g/ml) | 0.013–0.1 |
| 37 | retinol and related compounds ($\mu$g/ml) | 0.36–1.29 |
| 38 | xanthophyll ($\mu$g/ml) | 0.48–1.13 |
| 39 | total carotenoid ($\mu$g/ml) | 2.21–3.51 |
| 40 | $\alpha$-tocopherol ($\mu$g/ml) | 6.1–16.1 |
| 41 | $\beta$-tocopherol ($\mu$g/ml) | 0.06–0.2 |
| 42 | $\delta$-tocopherol ($\mu$g/ml) | 0.55–4.1 |
| 43 | $\gamma$-tocopherol ($\mu$g/ml) | 0.013–0.125 |
| 44 | cholesterol (mg/dl) | 130–280 |
| 45 | triglyceride (mg/dl) | 30–190 |
| 46 | total protein (g/dl) | 6–8.2 |
| 47 | albumin (g/dl) | 2.2–5.0 |
| 48 | albumin/globulin (g/dl) | 0.37–5.0 |
| 49 | globulin (g/dl) | 1–6.0 |
| 50 | glucose (mg/dl) | 78–115 |
| 51 | glutathione peroxidase (mg/dl) | 1.0–7.0 |
| 52 | coenzyme Q10 | 0.6–1.0 |
| 53 | superoxide dismutase [SOD] (U/ml) | 5–10 |
| 54 | catalase (U/ml) | 0.2–2.2 |

Figure 2:
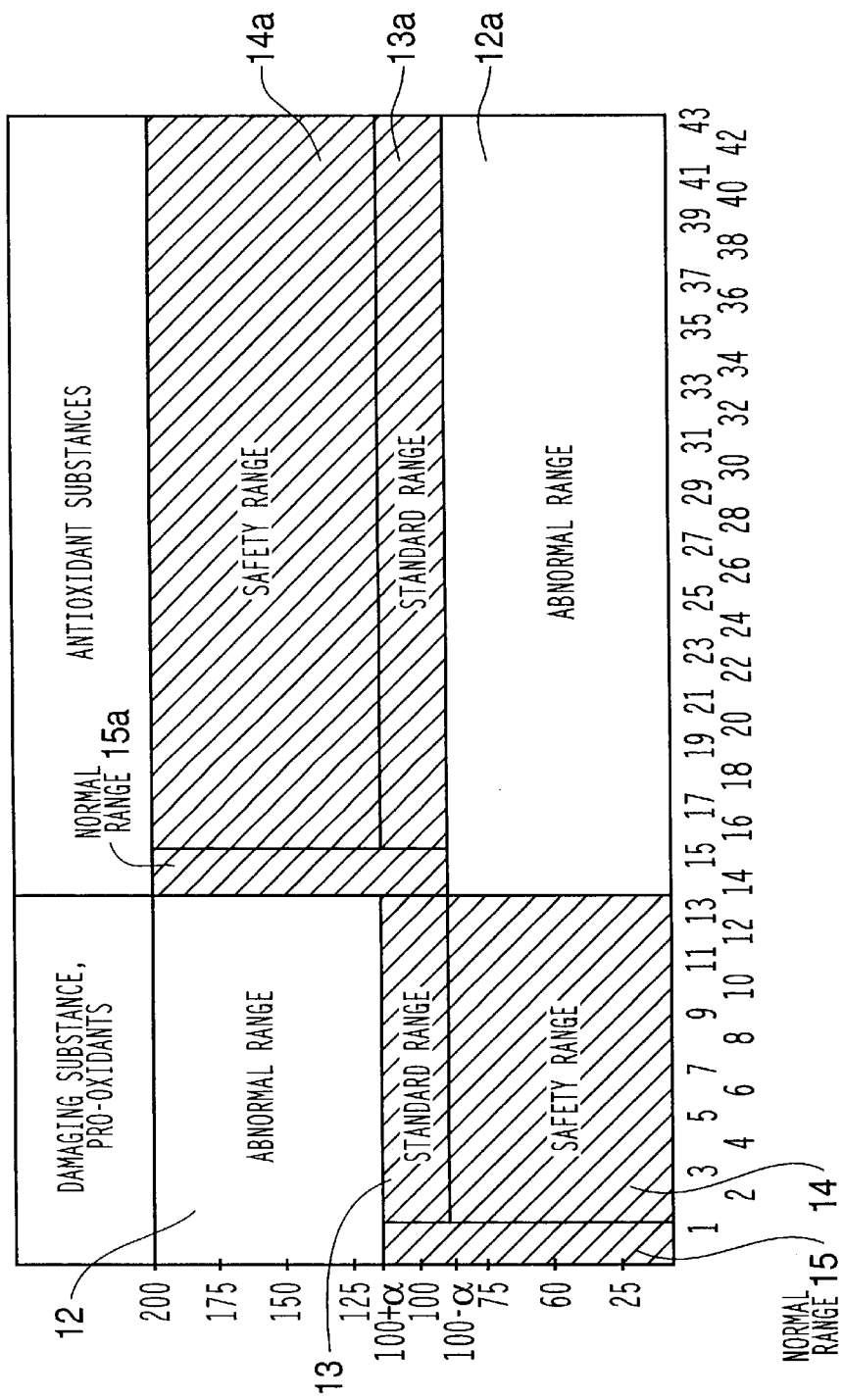
FIG. 2 is a chart used for assessing oxidative stress in accordance with the present invention, so as to assess as to which range the corrected values of individual indicator substances in a test subject are localized among the standard ranges, safety ranges, normal ranges and abnormal ranges.
Figure 3:
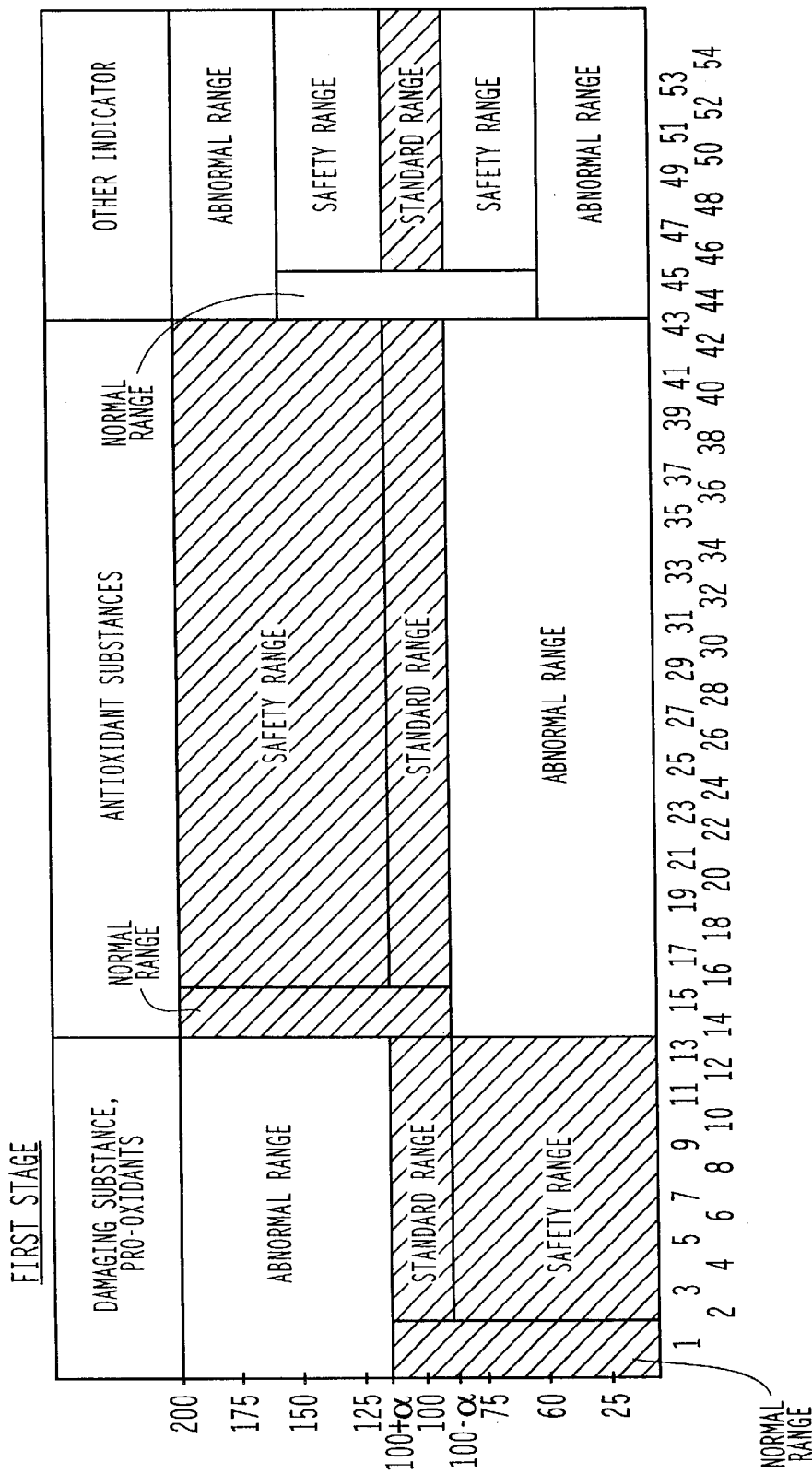
FIG. 3 is a chart depicting that the corrected values of individual indicator substances in a test subject represent 'the state with hypothetically zero oxidative stress' in the chart of FIG. 2.
Figure 4:
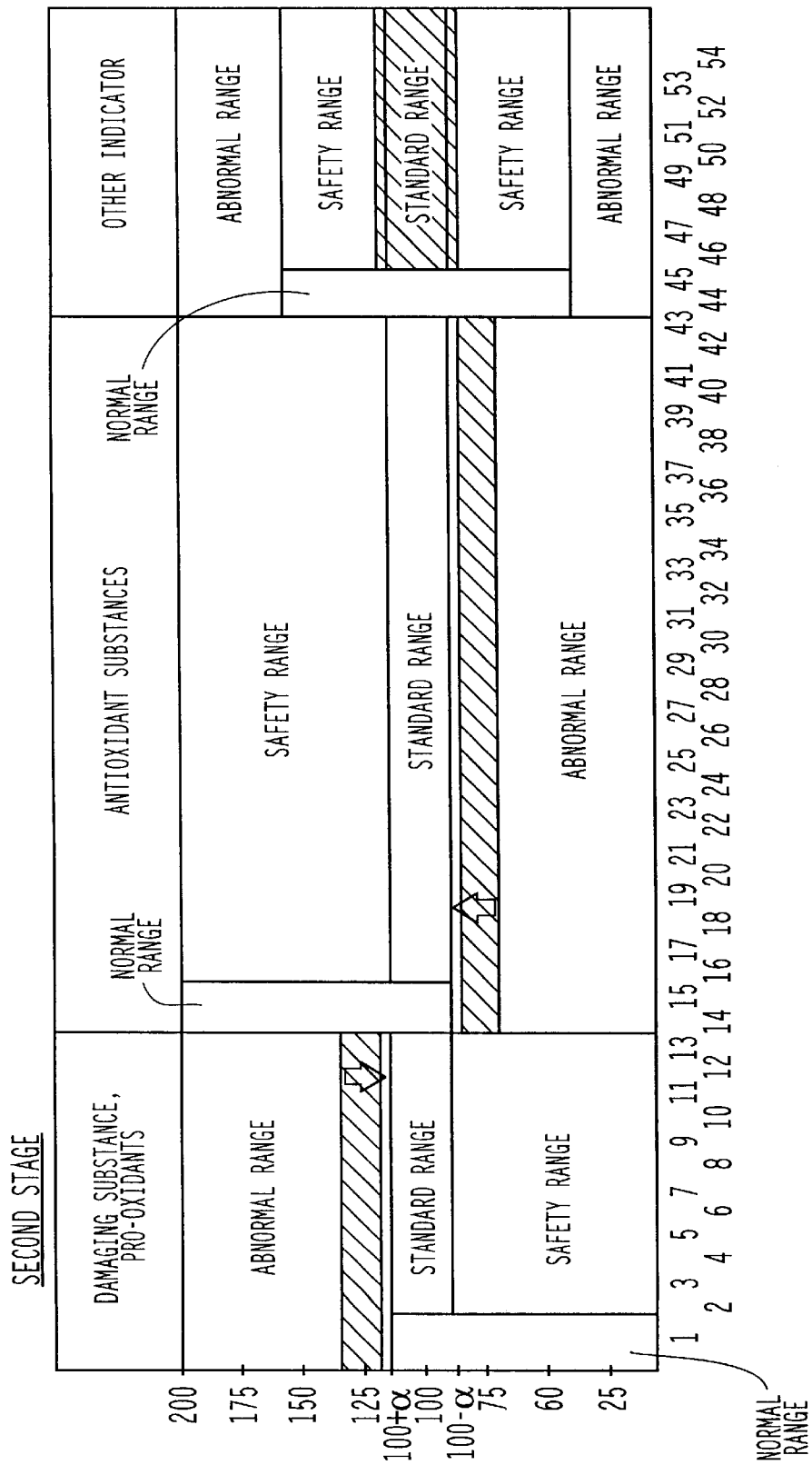
FIG. 4 is a chart depicting that the corrected values of individual indicator substances in a test subject represent 'the state with minimal oxidative stress' in the chart of FIG. 2.
Figure 5:
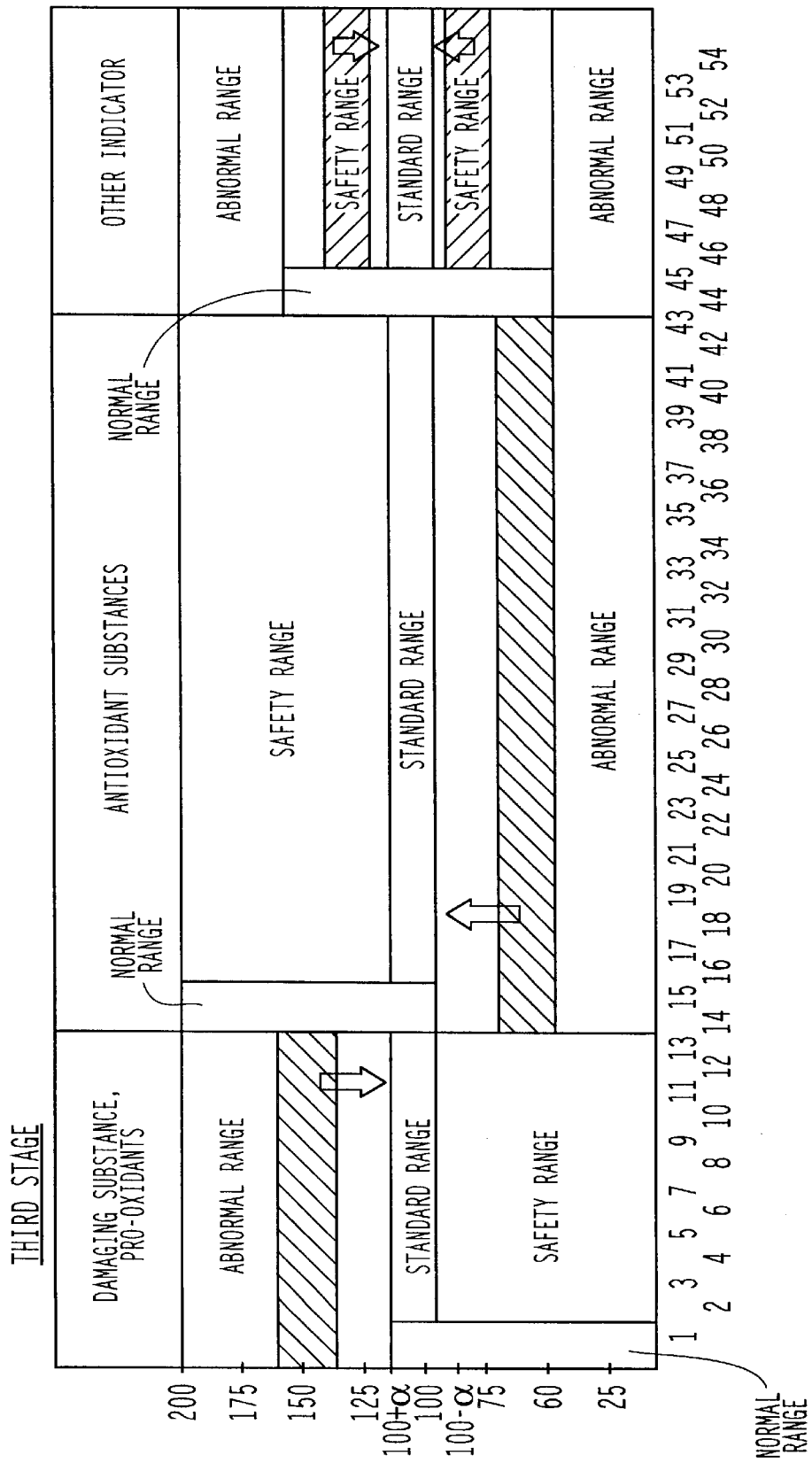
FIG. 5 is a chart depicting that the corrected values of individual indicator substances in a test subject represent 'the state with weak oxidative stress' in the chart of FIG. 2.
Figure 6:
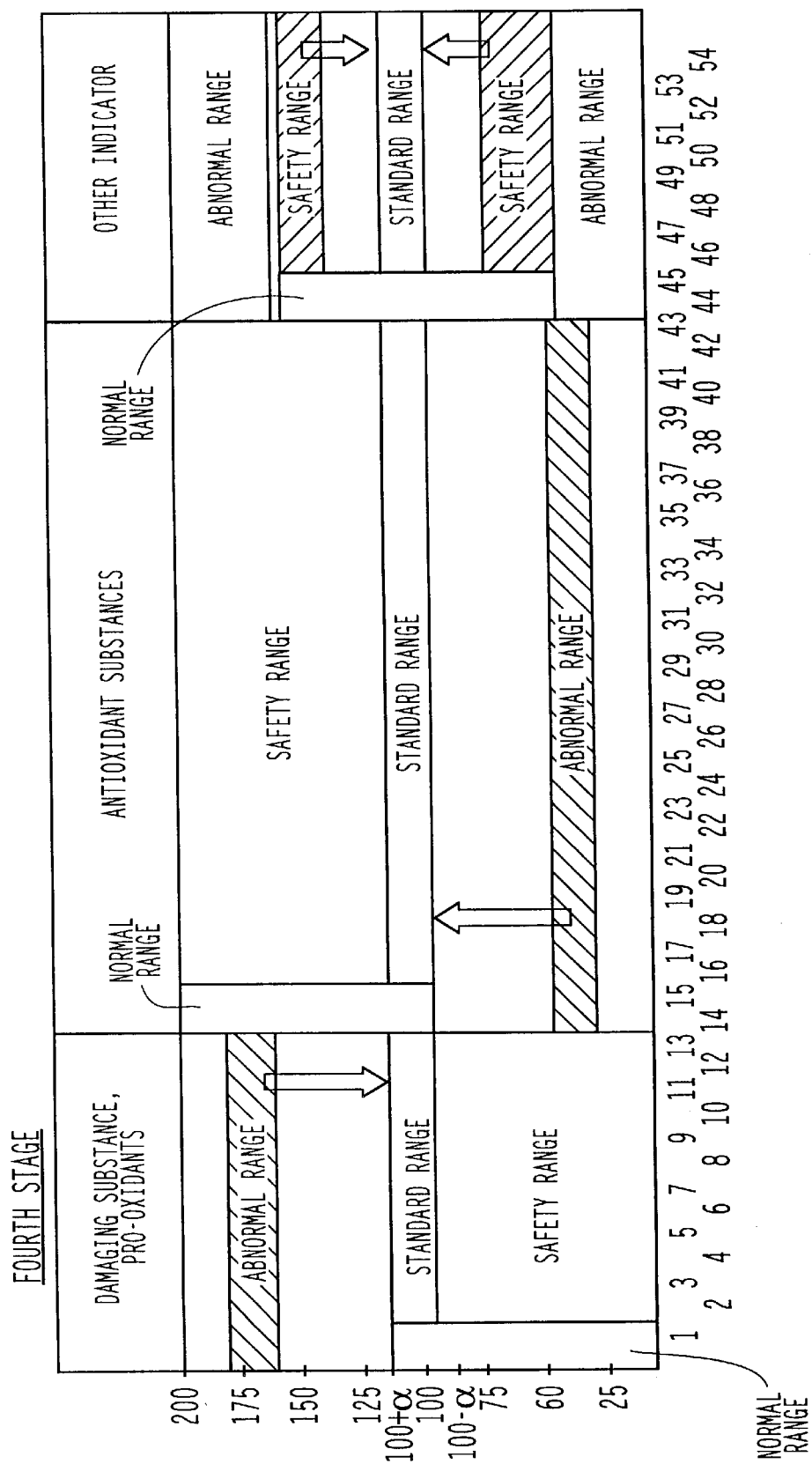
FIG. 6 is a chart depicting that the corrected values of individual indicator substances in a test subject represent 'the state with regular oxidative stress' in the chart of FIG. 2.
Figure 7:
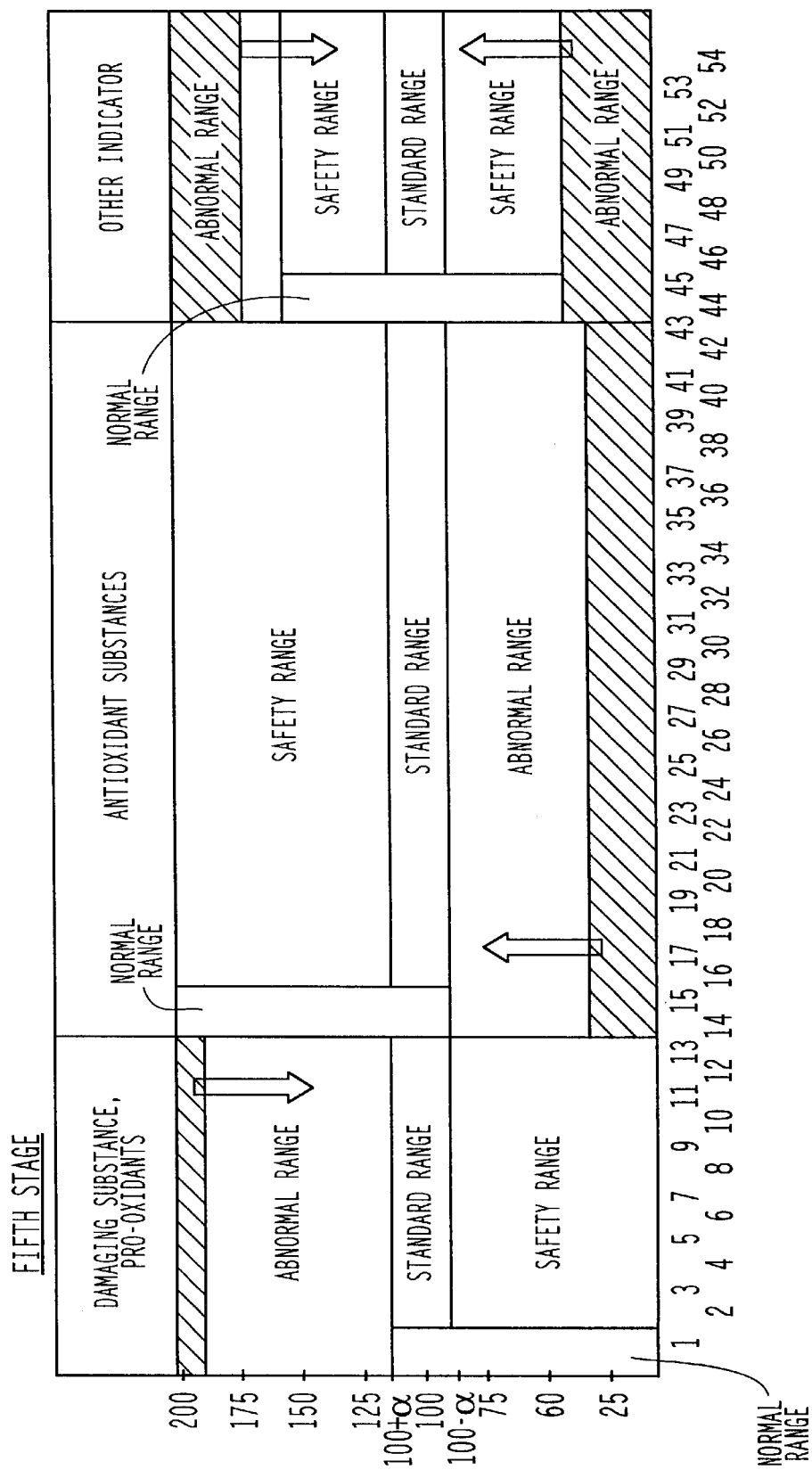
FIG. 7 is a chart depicting that the corrected values of individual indicator substances in a test subject represent 'the state with severe oxidative stress' in the chart of FIG. 2.

In the assessment chart of FIG. 2 for assessing oxidative stress, standard values are scaled as 100 at the center of the ordinate, while damaging substances and antioxidants are shown in the abscissa; and abnormal ranges 12, 12a, standard ranges 13, 13a, safety ranges 14, 14a and normal ranges 15, 15a are also shown in the chart.

EXAMPLE 2

Green tea powder extract (1 kg), ground tea (0.3 kg), catechin (0.05 kg) extracted from green tea, lemon juice powder (1 kg), beer yeast powder (1 kg) and cabbage powder (1 kg), all containing water-soluble antioxidants, were mixed together and processed into a tablet of 500 g/tablet at a total yield of 7 kg. This tablet was used as a supplement for supplementing water-soluble antioxidants. The analytical values of the supplement were as follows per 100 g; vitamin C 80 mg; vitamin $B_1$ 3 mg; vitamin $B_2$ 1 mg; effective vitamin A 10 mg. The superoxide radical scavenging activity thereof was determined by electron spin resonance spectroscopy, and found to be 9500 units/g.

Assessment is made by using the charts as shown in FIG. 1 to FIG. 7 for assessing oxidative stress. When it is demonstrated that a water-soluble antioxidant is deficient in a test subject, the test subject incorporates the supplement of the water-soluble antioxidant as prepared in the present example, to eliminate the deficiency appropriately in a simple procedure.

EXAMPLE 3

Carrot powder (1 kg), soybean powder (2 kg), black sesame paste (0.1 kg), green tea catechin (0.05 kg) and tomato powder (2 kg), all containing fat-soluble antioxidants, were mixed together and processed into a tablet of 500 mg/tablet at a total yield of 4.9 kg. This tablet was used as a supplement for supplementing fat-soluble antioxidants. The analytical values of the supplement were as follows on per 100 g basis; effective vitamin A 5.0 mg; vitamin $B_1$ 0.6 mg; vitamin $B_2$ 1 mg; vitamin C 60 mg; and vitamin E 9 mg. The superoxide radical scavenging activity of this tablet was determined by electron spin resonance spectroscopy to be 5500 units/g.

Assessment is made by using the charts as shown in FIG. 1 to FIG. 7 for assessing oxidative stress. When it is demonstrated that a fat-soluble antioxidant is deficient in a test subject, the test subject incorporates the supplement of the fat-soluble antioxidant as prepared in the present example to eliminate the deficiency appropriately in a simple procedure.

EXAMPLE 4

Green tea catechin (0.1 kg), green tea powder extract (1 kg), black sesame paste (0.1 kg), soybean powder (2 kg), beer yeast powder (1 kg), oyster extract (1 kg) and sea weed kombu powder (1 kg), all containing micronutrient minerals as the component of antioxidant enzymes, were mixed together and processed into a tablet of 500 mg/tablet at a total yield of 6 kg. This tablet was used as a supplement for supplementing the micronutrient minerals as the component of antioxidant enzymes. The analytical values of the supplement were as follows, on per 100g basis; vitamin $B_1$ 3 mg; vitamin C 7 mg; vitamin E 2 mg; copper (Cu) 14.9 mg; zinc (Zn) 87.8 mg; selenium (Se) 0.03 mg; manganese (Mn) 0.5 mg. The superoxide radical scavenging activity of this supplement was determined by electron spin resonance spectroscopy, and found to be 5000 units/g.

Assessment is made by using the charts as shown in FIG. 1 to FIG. 7 for assessing oxidative stress. When it is demonstrated that an antioxidant enzyme is deficient in a test subject, the test subject incorporates the supplement of the antioxidant enzyme as prepared in the present example to eliminate the deficiency appropriately in a simple procedure.

In the examples 2, 3 and 4 mentioned above, the antioxidant supplements were individually prepared as tablets. But these supplements may be prepared as powders, granules or as other molded forms. Additionally, two or more antioxidant supplements can be enveloped as a mixture or molded as a complex.

Although the present invention has been described with reference to the particular specific components, it should be understood that appropriate changes and modifications may be made within the spirit and scope of the invention, as defined in the appended claims.

What is claimed is:

1. A method for assessing oxidative stress in humans, comprising;

preparing a chart for assessing oxidative stress, wherein a numerical figure representing the degree of excess or deficiency of an indicator substance indicating oxidative stress in humans is shown in the ordinate and a numerical figure corresponding to the standard value recovered from normal subjects is also shown in the ordinate, and wherein the items of such indicator substances are grouped in damaging substances, water-soluble antioxidants, fat-soluble antioxidants, and antioxidant enzymes, to be shown in the abscissa;

numerically representing the measured value of each indicator substance indicating the extent of oxidative stress in humans from serum measurement of the test subject on the basis of the standard value of the indicator substance in normal subjects; and recording the resulting numerical figure of the indicator substance on the said chart for assessing oxidative stress.

2. A method for assessing oxidative stress in humans according to claim 1, wherein the indicator substance includes a damaging substance composed of at least one or more of serum malondialdehyde, 4-hydroxy nonenal, hydroperoxide, urine 8-hydroxy deoxyguanosine (nucleic acid) and a combination of malondialdehyde and 4-hydroxy nonenal; a water-soluble antioxidant consisting of at least one or more of ascorbic acid, thiols, uric acid, and bilirubin; a fat-soluble antioxidant consisting of at least one or more of lutein, zeaxanthin, cryptoxanthin, lycopene, carotenes, retinol and tocopherols; and an antioxidant enzyme consisting of at least one or more of coenzyme Q10, superoxide dismutase, catalase and glutathione peroxidase.

3. A method for assessing oxidative stress in humans, comprising;

preparing a chart for assessing oxidative stress, wherein a numerical figure representing the degree of excess or deficiency of an indicator substance indicating oxidative stress in humans is shown in the ordinate and a numerical figure corresponding to the standard value recovered from normal subjects is also shown in the ordinate; wherein the items of such indicator substances are grouped in damaging substances, water-soluble antioxidants, fat-soluble antioxidants and antioxidant enzymes to be shown in the abscissa; and wherein the standard range of each indicator substance is defined and arranged in the ordinate following the scale of numerical figures in the ordinate;

numerically representing the measured value of each indicator substance indicating the extent of oxidative stress in humans from serum measurement of the test subject on the basis of the standard value of the indicator substance in normal subjects; and recording the resulting numerical figure of the indicator substance on the said chart for assessing oxidative stress.

4. A method for assessing oxidative stress in humans according to claim 3, wherein the indicator substance includes a damaging substance composed of at least one or more of serum malondialdehyde, 4-hydroxy nonenal, hydroperoxide, urine 8-hydroxy deoxyguanosine (nucleic acid) and a combination of malondialdehyde and 4-hydroxy nonenal; a water-soluble antioxidant consisting of at least one or more of ascorbic acid, thiols, uric acid and bilirubin; a fat-soluble antioxidant consisting of at least one or more of lutein, zeaxanthin, cryptoxanthin, lycopene, carotenes, retinol and tocopherols; and an antioxidant enzyme consisting of at least one or more of coenzyme Q10, superoxide dismutase, catalase and glutathione peroxidase.

5. A method for assessing oxidative stress in humans, comprising;

preparing a chart for assessing oxidative stress, wherein a numerical figure representing the degree of excess or deficiency of an indicator substance indicating oxidative stress in humans is shown in the ordinate and a numerical figure corresponding to the standard value recovered from normal subjects is also shown in the ordinate; wherein the items of such indicator substances are grouped in damaging substances, water-soluble antioxidants, fat-soluble antioxidants, and antioxidant enzymes to be shown in the abscissa; and wherein the standard range, safety range, normal range and abnormal range of each indicator substance are defined and arranged in the ordinate, following the scale of numerical figures in the ordinate;

numerically representing the measured value of each indicator substance indicating the extent of oxidative stress in humans from serum measurement of the test subject on the basis of the standard value of the indicator substance in normal subjects; and recording the resulting numerical figure of the indicator substance on the said chart for assessing oxidative stress.

6. A method for assessing oxidative stress in humans according to claim 2, wherein the indicator substance includes a damaging substance composed of at least one or more of serum malondialdehyde, 4-hydroxy nonenal, hydroperoxide, urine 8-hydroxy deoxyguanosine (nucleic acid) and a combination of malondialdehyde and 4-hydroxy nonenal; a water-soluble antioxidant consisting of at least one or more of ascorbic acid, thiols, uric acid and bilirubin; a fat-soluble antioxidant consisting of at least one or more of lutein, zeaxanthin, cryptoxanthin, lycopene, carotenes, retinol and tocopherols; and an antioxidant enzyme consisting of at least one or more of coenzyme Q10, superoxide dismutase, catalase and glutathione peroxidase.

* * * * *